United States Patent [19]

Pilesi et al.

[11] 4,326,421
[45] Apr. 27, 1982

[54] CONTINUOUS PROOFLOADER

[75] Inventors: William D. Pilesi, Monroeville; Harry J. Trautmann, Pittsburgh, both of Pa.

[73] Assignee: Koppers Company, Inc., Pittsburgh, Pa.

[21] Appl. No.: 115,094

[22] Filed: Jan. 24, 1980

[51] Int. Cl.³ .............................................. G01N 3/20
[52] U.S. Cl. .................................................... 73/852
[58] Field of Search ........................... 73/849, 851, 852

[56] References Cited

U.S. PATENT DOCUMENTS 3,158,021 11/1964 Walters et al. ........................ 73/852
3,194,063 7/1965 McKean ................................ 73/852

FOREIGN PATENT DOCUMENTS 1466741 3/1977 United Kingdom .
653538 3/1979 U.S.S.R. ............................... 73/849

*Primary Examiner*—Anthony V. Ciarlante
*Attorney, Agent, or Firm*—Donald M. MacKay; Oscar B. Brumback

[57] ABSTRACT

An apparatus for determining the presence or absence of a predetermined minimum flexural strength and stiffness of a relatively rigid material, said apparatus comprising:
a frame, a pair of flexure means, each flexure means affixed on opposite sides and ends of a support means affixed to said frame, and equidistant from a fulcrum means for said support, said fulcrum means affixed to said frame with a pivot point at the midpoint thickness of the material to be tested, a pair of guide means, each guide means affixed to said frame equidistant from said fulcrum means and positioned on opposite sides of and apart from said flexure means whereby the material to be tested is guided between the flexure means and guide means in a substantially horizontal path, a load means affixed to said frame for applying a predetermined force to said support means whereby the flexure means deflects the relatively rigid material, and sensor means affixed to said frame for detecting the amount of deflection of said material.

7 Claims, 5 Drawing Figures

CONTINUOUS PROOFLOADER

BACKGROUND OF THE INVENTION

This invention relates to an apparatus for continuously assessing the flexural strength and stiffness of relatively rigid materials such as wood and particularly materials which have been joined end to end by means of an adhesive.

Laminated wooden beams and arches are typically manufactured from laminates whose cross-sections nominally range from 1"×4" to 2"×12" and whose lengths vary up to 165' (limited by manufacturing space). Lumber is trimmed to remove certain defects which are located near the ends so random lengths result. It is possible to use this lumber by cutting end joints and gluing these ends together. Quality control requirements of the AITC (American Institute for Timber Construction) dictate, however, that random end joint samples be tested to a required strength. In addition, further requirements stipulate that no two end joints located in the tension zone of a beam or anywhere in a tension member be stacked within six inches of each other in adjacent laminations in a laminated product because of the potential for a weak end joint that has not been verified by proofloading.

If all end joints could be individually tested and minimum strength established for the joint, the AITC requirements for stacked joints in the tension zone could be waived because the joint would have been proofloaded. In addition, the establishment of a minimum flexural strength for individual joints would assure the manufacturer that in meeting the design specifications he can minimize his risk of product liability.

Not only would mismanufactured end joints be discovered immediately, other natural strength reducing characteristics would be better controlled and also, the variable stiffness along the length of the lamination would be monitored. The system would therefore greatly improve the structural reliability of the end product. Immediate detection of defective end joints has the advantage of being more economical than if they are detected later in the manufacturing process.

BRIEF DESCRIPTION OF THE INVENTION

It has now been discovered that relatively rigid materials such as wood, particle board, flake board, reinforced plastics, composite building materials, and particularly end joints of laminated wooden products can be tested for flexural strength and stiffness by means of an in line apparatus coupled with the manufacturing operation which enables one to obtain the aforesaid benefits. More particularly, the flexural strength and stiffness of a relatively rigid material is tested by means of an apparatus comprising two flexure means or rollers affixed to a yoke assembly to produce a couple loading on the relatively rigid material producing opposite bending stresses and deflections on said material in both directions simultaneously. As material is fed through the machine it is deflected downward as it passes under the first roll and upward as it passes over the second roll of the couple producing yoke. The resultant deflection is averaged and measured by the movement of the yoke. This deflection has a maximum value commensurate with the structural capacities of the material passing between the rolls. Should the deflection exceed the maximum preset amount for the size material being tested, the material would be deemed below required stiffness and strength and appropriately marked so that it would not be incorporated into a laminated product. Weak end joints would appear to the apparatus as an extremely flexible or low stiffness member. The simplicity of the couple yoke assembly to produce reverse bending is its ability to mechanically average the loading required in opposite directions, as well as providing an average deflection. The average deflection can then be correlated to the average strength and stiffness in both directions of the lamination. Should a poor end joint or weak material enter the machine, an excessive deflection would be indicated and a means activated to mark the weak material such as with a special color dye. Moreover, the apparatus enables one to test for both tensile and compressive strength. Because of reverse bending both upper and lower surfaces of the laminate are subjected to tension and compression stresses. This concept is important because in testing an end joint both surfaces should be tested in tension.

More particularly, the apparatus determines the presence or absence of a predetermined minimum flexural strength or stiffness of a relatively rigid material and comprises:

a frame, a pair of flexure means, each flexure means affixed on opposite sides and ends of a support means affixed to said frame, and equidistant from a fulcrum means for said support, said fulcrum means affixed to said frame with a pivot point at the midpoint thickness of the material to be tested, a pair of guide means, each guide means affixed to said frame equidistant from said fulcrum means and positioned on opposite sides of and apart from said flexure means whereby the material to be tested is guided between the flexure means and guide means in a substantially horizontal path, a load means affixed to said frame for applying a predetermined force to said support means whereby the flexure means deflects the relatively rigid material, and sensor means affixed to said frame for detecting the amount of deflection of said material.

DETAILED DESCRIPTION OF THE INVENTION

Figure 1:
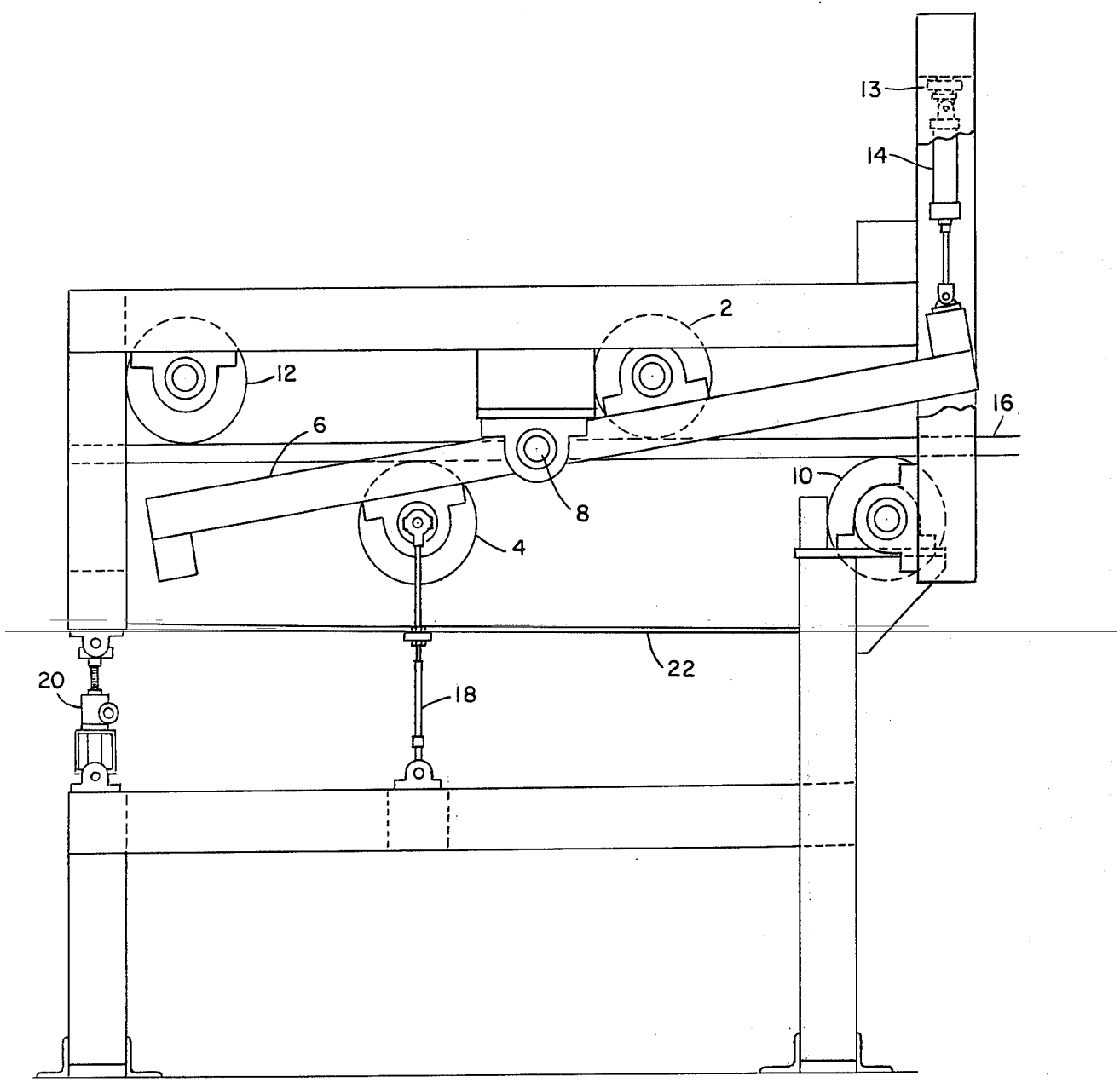
FIG. 1 is a side view of the apparatus of the invention.

Referring now to the drawings and particularly FIG. 1, a pair of flexure means are shown as numerals 2 and 4 as wheels or rollers. The flexure means are affixed to a support means 6 which pivots from a fulcrum means 8. A fixed guide means 10 and a movable, adjustable guide means 12 are shown as wheels or rollers. A load means 14 is provided to apply a downward force to support 6 (which is measured by load cell 13) whereby a relatively rigid material such as wood is deflected by the action of flexure means 2 and 4. Flexure means 2 and 4 are positioned on opposite sides of support 6 and equidistant from fulcrum 8. Fulcrum 8 is positioned so that the pivot point of support 6 is located at the thickness midpoint of the relatively rigid material to be tested 16. As feed material 16 is fed between guide means 10 and 12, and flexure means 2 and 4, a predetermined load is applied at 14 to cause support 6 to pivot about fulcrum 8. Rollers 2 and 4 are caused to press against the relatively rigid material 16 with an equal but opposite force to deflect said material so as to determine the presence or absence of a desired flexural strength or stiffness. A sensor means 18 is affixed to flexure means 4 to measure the amount of deflection of material 16 so as to enable specimens having insufficient stiffness, i.e. that flex too much, to be identified and separated. Typically, a dye marking device, not shown, is incorporated to mark materials lacking the desired flexural strength and stiffness. An adjustment means 20 is provided for guide means 12 to enable feed materials of different thicknesses to be levelled in a substantially horizontal plane with the fulcrum 8 pivot point centered at the midpoint thickness of the feed material 16. A platform 22 catches feed materials which are broken by the flexure means, and a switch (not shown) turns off the apparatus.

The apparatus can be used to test the ultimate strength of an end joint by stopping the joint under one of the flexure means and applying a force sufficient to cause the joint to fail completely. The applied load 14 can be correlated to the strength of the joint. The rate at which the flexure force increases can be controlled by varying at a predetermined rate a set point of the hydraulic control unit 14 and the force at which the end joint fails can be recorded from the load cell signal.

Figure 2:
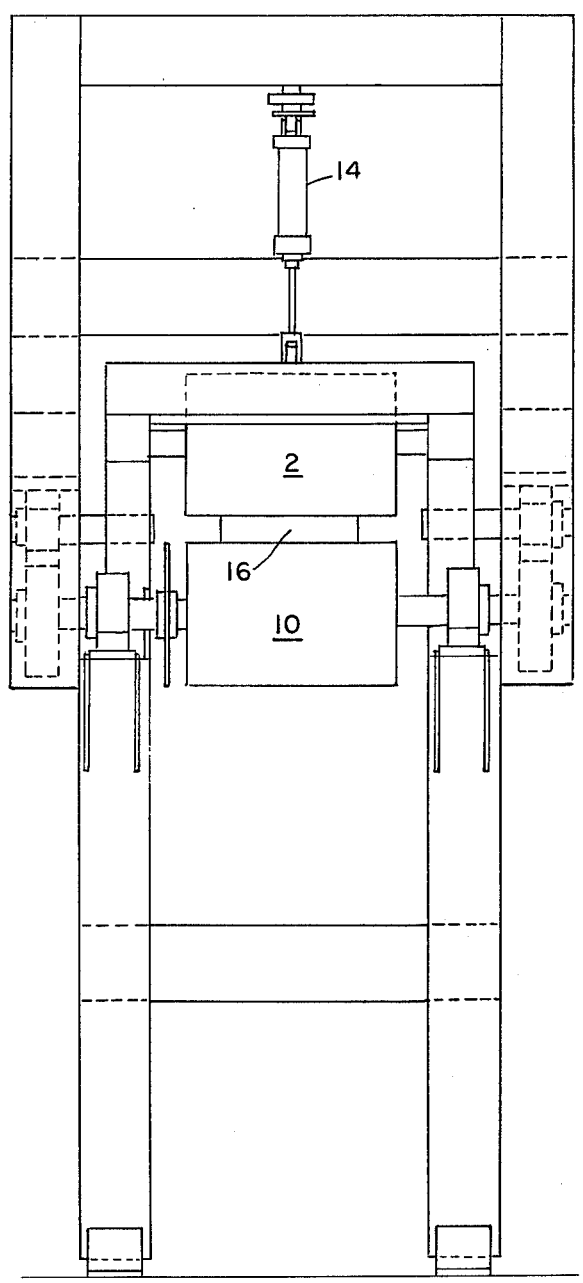
FIG. 2 is an end view of the feed end of the apparatus.

In FIG. 2 an end view of the apparatus is shown from the feed end. Board 16 is passed between flexure roll 2 and guide roll 10 with a force applied by load means 14.

Figure 3:
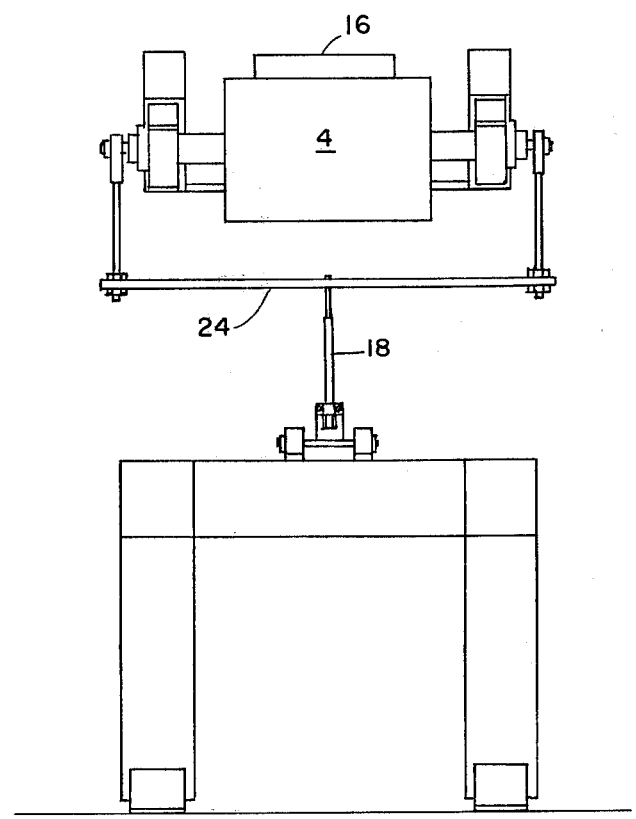
FIG. 3 is a center section view of the apparatus.

In FIG. 3 a center section is shown wherein sensor means 18 is connected to flexure roll 4 by means of a trapeze configuration 24.

Figure 4:
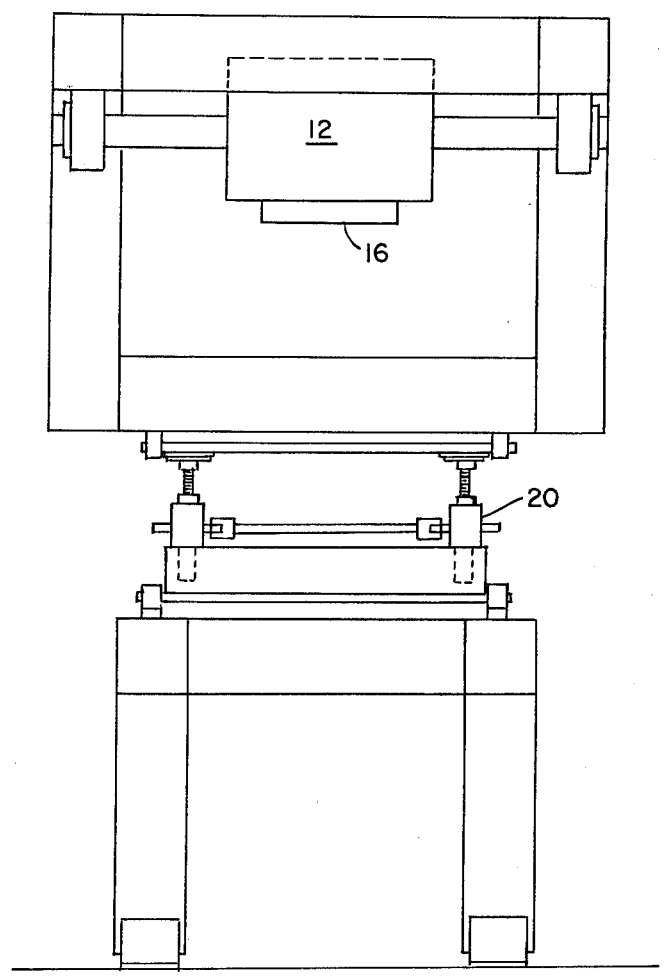
FIG. 4 is a view of the exit end of the apparatus.

In FIG. 4 the exit end of the apparatus is shown. Guide means 12 is regulated by adjustment means 20 to level board 16.

Figure 5:
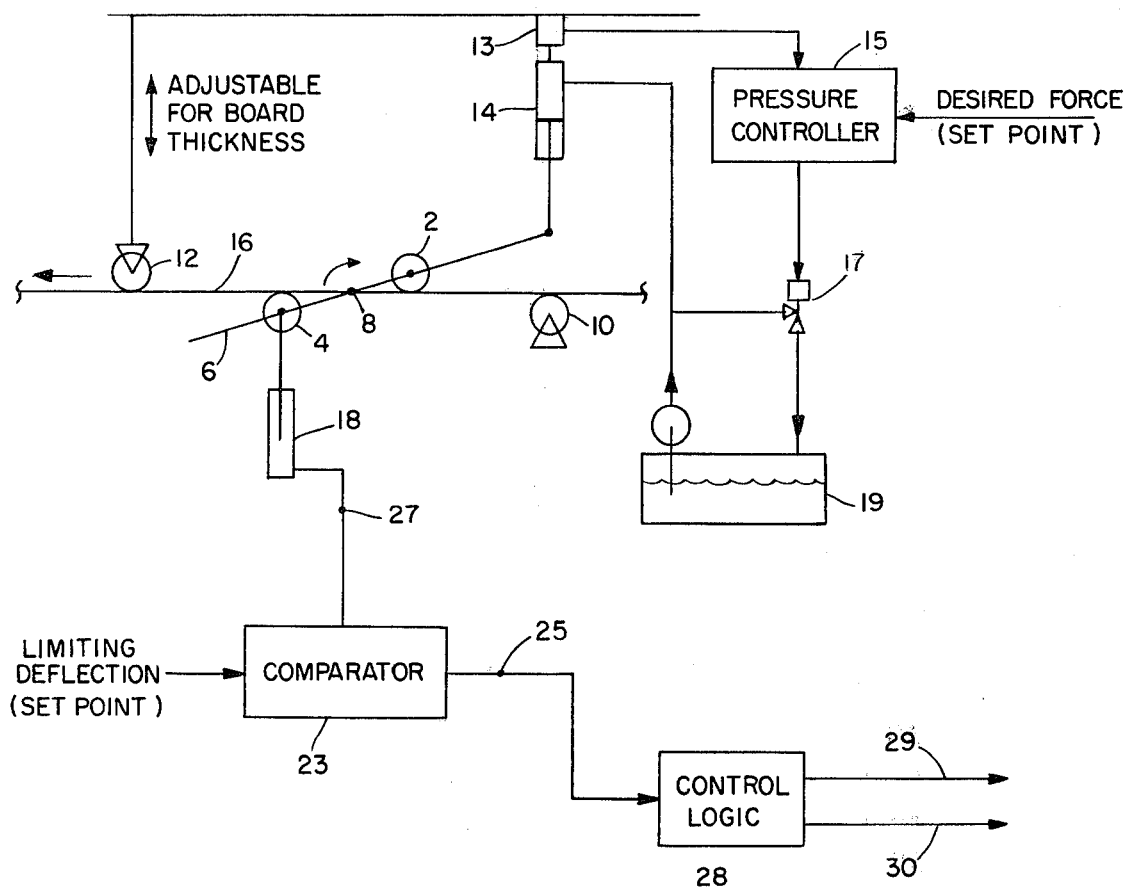
FIG. 5 is a schematic diagram of the apparatus controls.

In FIG. 5 a schematic of the apparatus control is shown. The desired pressure or force to be applied to the board 16 is set at pressure controller 15. An electrical signal to control valve 17 regulates hydraulic pressure from unit 19 which in turn activates hydraulic cylinder 14 to move frame 6. Load cell 13 signals pressure controller 15 of the load applied to board 16. Deflection transducer 18 transmits a signal proportional to the deflection of board 16 at the point of loading 4 to comparator 23. If the deflection recorded by transducer 18 exceeds a predetermined amount, comparator 23 signals a logic control 28 which signals via line 29 to reverse action of hydraulic cylinder 14, to stop feed of board 16, to sound an alarm and spray board of a suitable color if deflection is excessive. If the amount of deflection is within the limit set, logic control 28 signals via line 30 to spray the board at intervals with a suitable color indicating acceptance.

While the invention has been illustrated by means of preferred embodiments and the best mode, variations and equivalents may occur to one of ordinary skill in the art. Accordingly, the invention should be limited only by the appended claims.

What is claimed is:

1. A proofloader for continuously determining the presence or absence of a predetermined minimum flexural strength and stiffness in a relatively rigid material such as wood along its path of travel through the loader comprising a frame through which said material travels;

fulcrum means affixed to said frame and having a pivot point at the mid-point of the thickness of the material in its path of travel;

support means rotatable about said pivot point as a fulcrum for said support;

a pair of flexure means, each flexure means being affixed to opposite ends and on opposite sides of said support for applying a flexure force on opposite faces of said material as the material travels between the flexure means;

a pair of guide means, each guide means being affixed to said frame equidistant from said fulcrum means and positioned apart from said flexure means and on opposite sides of the path of the material whereby the guide means restrains the material to travel between the flexure means and guide means in a substantially horizontal path and to resist the force applied to the material by the adjacent flexure means;

load means affixed to said frame for applying a predetermined force to said support means whereby each flexure means deflects the material in an equal but different vertical direction from the horizontal path and the force is opposed by a respective guide means; and sensor means affixed to said frame for detecting the amount of deflection of said material as the material travels from one guide means to the other.

2. The apparatus of claim 1 additionally comprising a feed means for feeding a relatively rigid material between the pair of flexure means.

3. The apparatus of claim 1 wherein the flexure means comprises a wheel or roller.

4. The apparatus of claim 1 wherein the guide means comprises a wheel or roller.

5. The apparatus of claim 1 wherein the guide means are positioned at a greater distance from the fulcrum means than the flexure means.

6. The apparatus of claim 1 wherein the sensor means is connected to a flexure means.

7. The apparatus of claim 1 wherein there is provided adjustment means for a guide means to permit the guide means to be moved vertically to accommodate relatively rigid materials of different thicknesses and hold them in a substantially horizontal plane, and at the same time positioning the fulcrum at the midheight of the material being tested.

* * * * *